United States Patent [19]

Phlipot

[11] Patent Number: 5,344,461
[45] Date of Patent: Sep. 6, 1994

[54] MODULAR IMPLANT PROVISIONAL

[75] Inventor: Jack W. Phlipot, Warsaw, Ind.

[73] Assignee: Zimmer, Inc., Warsaw, Ind.

[21] Appl. No.: 16,915

[22] Filed: Feb. 12, 1993

[51] Int. Cl.$^5$ .............................................. A61F 2/38
[52] U.S. Cl. .......................................... 623/20; 623/18
[58] Field of Search ............................. 623/20, 18, 23

[56] References Cited

U.S. PATENT DOCUMENTS

| | | | |
|---|---|---|---|
| 4,728,332 | 3/1980 | Albrektsson | 623/20 |
| 4,731,086 | 3/1988 | Whiteside et al. | 623/20 |
| 4,936,847 | 6/1990 | Mangnelli | 623/20 |
| 4,944,757 | 7/1990 | Martinez et al. | 623/20 |
| 5,019,103 | 5/1991 | Van Zile et al. | 623/20 |
| 5,047,058 | 9/1991 | Roberts et al. | 623/20 |
| 5,071,438 | 12/1991 | Jones et al. | 623/20 |
| 5,080,675 | 1/1992 | Lawes et al. | 623/20 |
| 5,152,797 | 10/1992 | Luckman et al. | 623/20 |
| 5,201,769 | 4/1993 | Schurer | 623/20 |

Primary Examiner—David Isabella
Attorney, Agent, or Firm—Todd A. Dawson

[57] ABSTRACT

A rotating dovetail attachment mechanism for connecting a modular provisional augmentation block to the distal surface of a provisional tibial tray. The augmentation block has lateral components which contact a vertical surface on a prepared bone. The rotating dovetail attachment mechanism permits the block to be used with a stemmed tibial implant provisional by rotating the lateral components of the augmentation block around the stem during connection of the provisional block to the provisional tibial component.

3 Claims, 3 Drawing Sheets

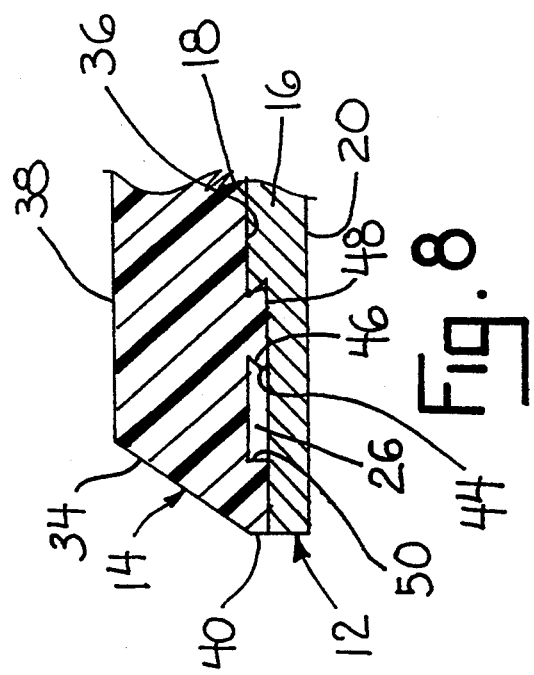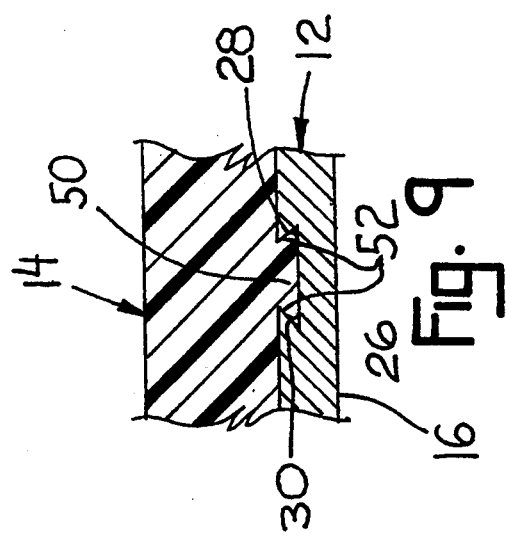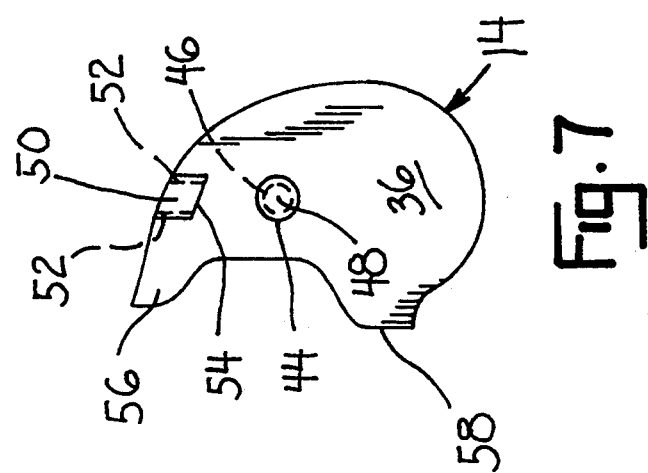

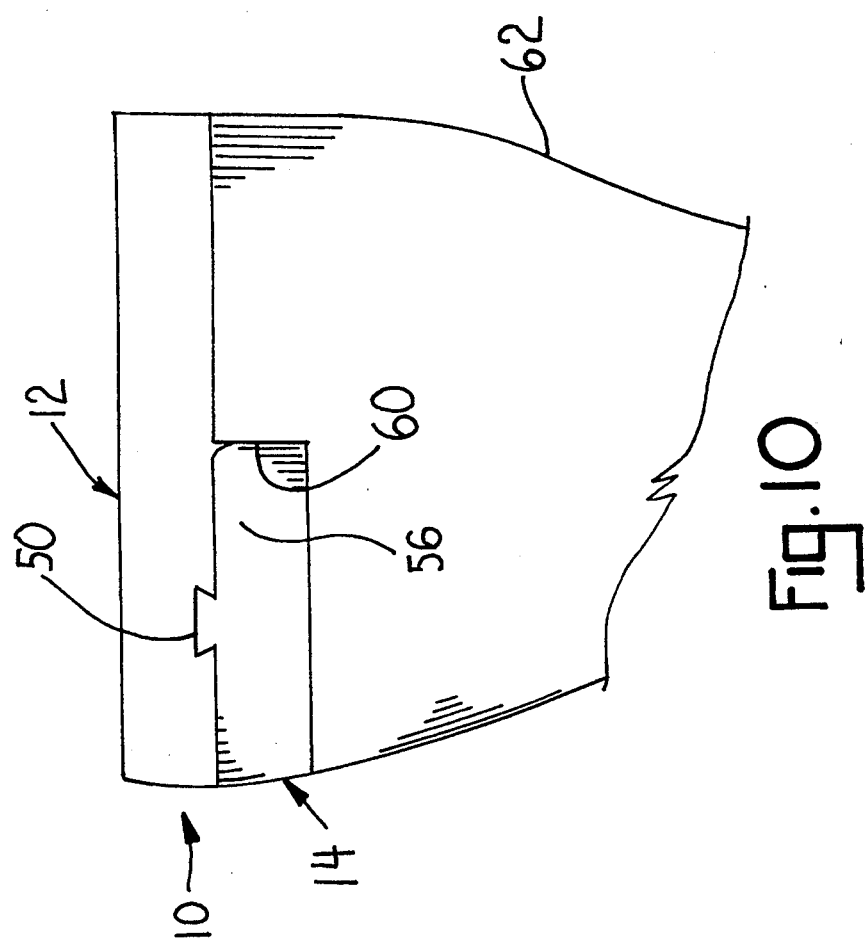

MODULAR IMPLANT PROVISIONAL

FIELD OF THE INVENTION

This invention relates to prosthetic implants and has special relevance to a prosthetic device having modular attachments which are connectable using a rotating dovetail attachment mechanism. Preferably the prosthetic device is a implant provisional.

BACKGROUND OF THE INVENTION

Implant provisionals are used during joint replacement surgery to test the surgeons reshaping of the supporting bone and to provide a trial alignment. While the actual implant could be used, it is more acceptable to use an implant provisional for such tests to prevent damage to the actual implant. In order for the surgeon to accurately gauge the fit and alignment of the final prosthesis, the implant provisional must be identical in dimension to the actual implant. Any variance in dimension between the implant and provisional could result in a less than optimal fit of the implant. Some implants, particularly tibial components, have a set of modular augments which may be connected to the bone contacting side of the tibial component to angulate the tibial tray sufficient to properly align a worn knee. To properly gauge the fit and alignment of the implant, the provisional must also include modular augmentation blocks. To provide ease of use, the provisional augmentation blocks are configured to slide on and off the provisional tibial component. The requirement to slide the provisional blocks on and off of the tibial component creates a problem in that the blocks may shift a small amount which may provide false information to a surgeon unaware of the shifting.

SUMMARY OF THE INVENTION

The rotating dovetail attachment mechanism for a provisional augmentation block of this invention solves the problems discussed above by providing augmentation blocks which have lateral components for contacting the prepared bone to prevent lateral shifting of the blocks. The rotating dovetail attachment mechanism permits the blocks to be used with a stemmed tibial implant provisional by rotating the lateral components of the augmentation blocks around the stem during connection of the provisional block to the provisional tibial component.

Accordingly, it is an advantage of the invention to provide for a novel provisional tibial implant with augmentation blocks.

Another advantage of the invention is to provide for a novel augmentation block for connection to a provisional tibial component.

Another advantage of the invention is to provide a rotating dovetail attachment mechanism for an augmentation block for a tibial component.

Other objects of the invention will become apparent upon a reading of the following description taken with the accompanying drawings.

BRIEF DESCRIPTION OF THE DRAWINGS

FIG. 7 is an elevational view of the provisional augmentation block of the invention.

FIG. 8 is a cross sectional view taken along line 8—8 of FIG. 6.

FIG. 9 is a cross sectional view taken along line 9—9 of FIG. 6.

FIG. 10 is an elevational view of the implant provisional with augmentation block in contact with the prepared proximal end of a tibia.

DESCRIPTION OF THE PREFERRED EMBODIMENT

Figure 1:
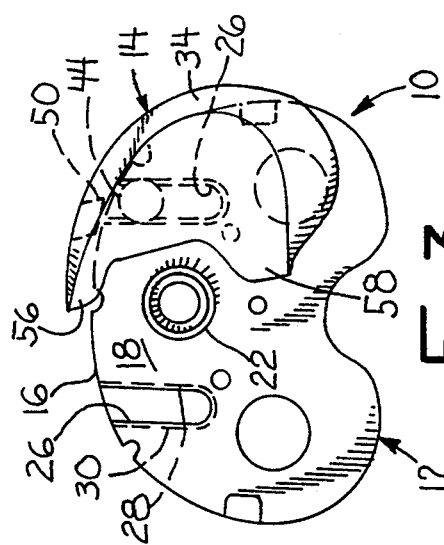
FIGS. 1 through 6 illustrate in sequence the rotational connection of the provisional augmentation block of the invention to the provisional tibial component.
Figure 4:
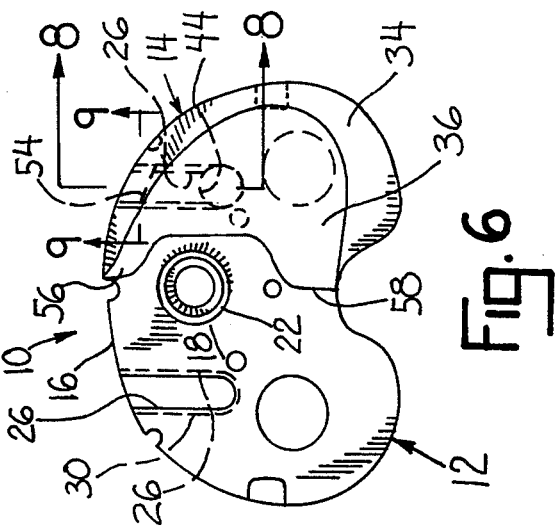

The preferred embodiment herein described is not intended to be exhaustive or to limit the invention to the precise form disclosed. Rather, it is chosen and described to best explain the invention so that others skilled in the art might utilize its teachings.

Referring now to the figures, implant provisional 10 consists of a tibial component 12 and modular augmentation blocks 14. For illustration purposes, only one augmentation block 14 is illustrated; however, in practice, a set of augmentation blocks would be provided to the surgeon each having a different thickness and angular orientation. With the set, the surgeon may build the optimum implant provisional for the patient. The use of augmentation blocks is known in the industry and is understood by one skilled in the art. For the ease of discussion, only the illustrated augmentation block 14 will be discussed.

Provisional tibial component 12 includes a tibial tray 16 having a bottom or distal surface 18. The upper or proximal surface 20 of the tibial tray 16 is configured to accommodate a bearing insert (not shown) for sliding engagement with the femoral component of the knee (also not shown). A post or stem 22 extends from tray 16 away from distal surface 18 and generally perpendicular to the tray 16. As is well known in the art, stem 22 is configured for insertion into the prepared intramedullary canal of the tibia. The anterior edge 24 of the provision tibial component 12 is arcuate. It should be understood that the terms anterior, posterior, distal, and proximal are commonly used and understood in the art as well as the specific relevance to the implant provisional. A slot 26 is formed in the distal surface 18 on each side of stem 22 extending from the anterior edge as illustrated and terminating in an arcuate end wall 27. Each slot 26 is formed with diverging side walls 28, 30 and a flat wall 32 which form a dovetail slot configuration. One slot 26 is illustrated in cross section in FIG. 9 to more fully illustrate the orientation of the slot and the dovetail shape. It should be understood that slots 26 are identical to one another.

Figure 6:
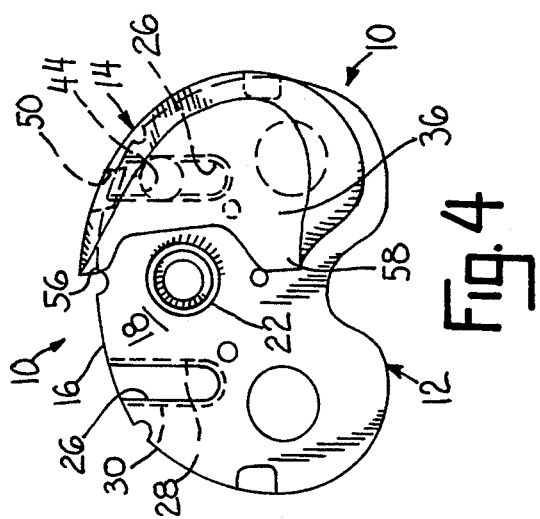

Modular augmentation blocks 14, only one shown, are shaped having an outer periphery 34 which is angled from the proximal surface 36 toward the distal surface 38 such that the edge of the proximal surface 40 of the outer periphery of the block 14 is in alignment with the edge of the distal surface 18 of the tibial tray 16. The outer periphery 34 follows the periphery of approximately one half of the tibial tray 16 as illustrated in FIG. 6. The distal surface of block 14 is substantially flat. A protrusion 44 extends transversely from proximal surface 36 and includes a diverging outer wall 46 and a flat wall 46. A cross section of protrusion 44 is illustrated in FIG. 8, from where it can be seen that the protrusion is generally dovetail in shape to substantially match the dovetail shaped slot 26 in the tibial tray 16. From the elevational view of FIG. 7, it is evident that the protrusion of 44 is generally round. A second protrusion 50 extends transversely from proximal surface 36 adjacent the anterior edge of the augmentation block 14. Protrusion 50 includes a pair of side walls 52 which diverge with distance from the proximal surface 36 of the augmentation block. As illustrated best in FIG. 9, the cross section of protrusion 50 is generally dovetail in shape and is configured for sliding accommodation within a slot 26. The posterior wall 54 of protrusion 50 generally follows the contour of the anterior edge of the block 14. Finally, augmentation block 14 includes an anterior extension 56 and a posterior extension 58 which extend laterally from block 14 as illustrated and define a gap therebetween. Each extension 56 and 58 terminates in a generally flat end wall at a midpoint of the tibial tray 16.

Figure 2:
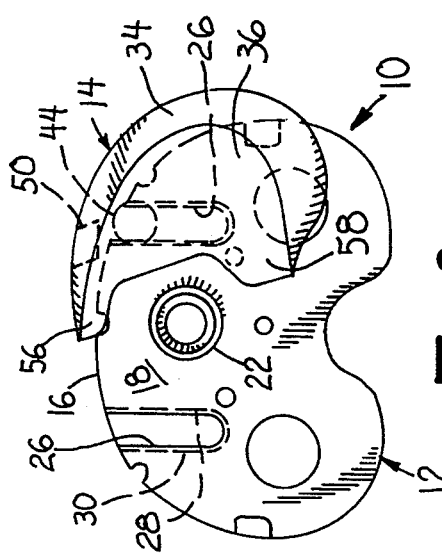
Figure 5:
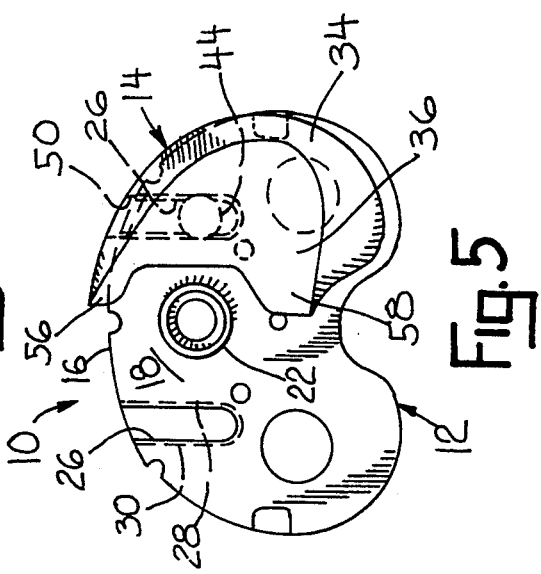
Figure 3:
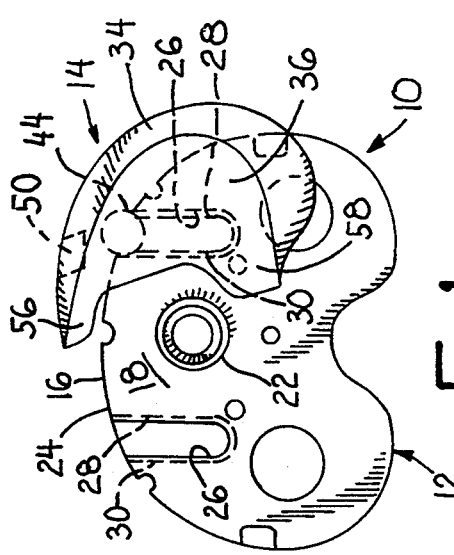

FIGS. 1 through 6 illustrate in progression the method of attaching the augmentation block 14 to the distal surface of the tibial tray 16. In the step illustrated in FIG. 1, protrusion 44 is inserted into a slot 26 of tibial tray 16. As illustrated, to accommodate extension 58, the augmentation block 14 is angled slightly relative to the tibial tray. The augmentation block 14 is slid posteriorly along slot 26 until protrusion 50 contacts the anterior wall of the tibial tray as illustrated in FIGS. 2 and 3). Next the augmentation block 14 is rotated such that the posterior wall of protrusion 50 follows the anterior wall of the tibial tray 16 until protrusion 50 is aligned with slot 26 (see FIG. 4). With protrusion 50 aligned in slot 26, the augmentation block 14 may be slid further laterally until protrusion 44 contacts the arcuate end wall of slot 26 (see FIGS. 5 through 9). At this point the augmentation block is fully seated. It should be noted that extensions 56 and 58 terminate at a mid-point on the tibial tray such that when the tibial tray and augmentation block are placed on the prepared tibia, the extensions would contact a vertical edge 60 of the prepared tibia bone 62 to thereby prevent lateral movement of the block 14 (see FIG. 10). The rotational connection of the augmentation block to the tibial tray is necessary so that extensions 58 may pass around the stem of the tibial tray.

It should be understood that the invention is not to be limited to the precise forms disclosed but may be modified within the keeping of the appended claims.

I claim:

1. A provisional tibial component for a knee joint prosthesis having modular augmentation block, the provisional tibial component comprising; a tibial tray having a proximal surface configured for contact with a bearing insert and a distal surface configured for contact with prepared bone surface, the tibial tray including an anterior surface and a posterior surface, a slot being formed in the distal surface extending from the anterior surface to the posterior surface, the slot including angled side walls, a stem portion extending generally transversely away from the distal surface of the tibial tray, the modular augmentation block including a proximal surface configured for contact with the distal surface of the tibial tray, a distal surface configured for contact with a prepared bone, a pair of protrusions extending from the proximal surface of the augmentation block toward the distal surface of the tibial tray and shaped to be slidably engaged within the slot of the tibial tray, the pair of protrusions being spaced apart, the augmentation block further including at least one lateral extension extending along the distal surface of the tibial tray and being configured to contact a prepared surface of an accommodating bone, one of the pair of protrusions constituting means for rotating the augmentation block relative to the tibial tray so that the extension may be positioned posterior to the stem.

2. The implant provisional of claim 1 wherein at least one of the pair of protrusions is round in cross section, each of the pair of protrusions including angled side walls shaped to complimentarily engage the angled side wall of the slot formed in the tibial tray.

3. A provisional tibial component for a knee joint prosthesis having modular augmentation block, the provisional tibial component comprising; a tibial tray having a proximal surface configured for contact with a bearing insert and a distal surface configured for contact with prepared bone surface, a stem portion extending generally transversely away from the distal surface of the tibial tray, the modular augmentation block including a proximal surface configured for contact with the distal surface of the tibial tray, a distal surface configured for contact with a prepared bone, the augmentation block further including at least one lateral extension extending along the distal surface of the tibial tray and being configured to contact a vertical surface of a prepared bone accommodating the tibial component and augmentation block, and connection means for attaching the augmentation block to the tibial tray such that the extension of the augmentation block is positioned posterior to the stem portion.

* * * * *